(12) United States Patent
Pommereau et al.

(10) Patent No.: US 9,427,524 B2
(45) Date of Patent: Aug. 30, 2016

(54) DRUG DELIVERY DEVICE WITH INTEGRATED EXTENDABLE/RETRACTABLE INFORMATION DISPLAY ELEMENT

(75) Inventors: Christian Pommereau, Frankfurt am Main (DE); Steffen Raab, Frankfurt am Main (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 315 days.

(21) Appl. No.: 13/259,160

(22) PCT Filed: Mar. 26, 2010

(86) PCT No.: PCT/EP2010/053966
§ 371 (c)(1),
(2), (4) Date: Dec. 21, 2011

(87) PCT Pub. No.: WO2010/112407
PCT Pub. Date: Oct. 7, 2010

(65) Prior Publication Data
US 2013/0006188 A1   Jan. 3, 2013

(30) Foreign Application Priority Data
Mar. 30, 2009   (EP) .................................. 09004571

(51) Int. Cl.
| A61M 5/178 | (2006.01) |
| G09F 3/02 | (2006.01) |
| G09F 3/00 | (2006.01) |
| G09F 3/20 | (2006.01) |
| G09F 11/30 | (2006.01) |
| A61M 5/31 | (2006.01) |

(52) U.S. Cl.
CPC .............. *A61M 5/178* (2013.01); *G09F 3/02* (2013.01); *G09F 3/0289* (2013.01);
(Continued)

(58) Field of Classification Search
CPC ................. A61M 2005/3126; A61M 5/3129; A61M 2005/3125; G09F 11/30; G09F 3/0289; G09F 3/0295; G09F 3/205; G09F 3/02
USPC ............... 604/189; 206/459.1, 459.5; 59/189
See application file for complete search history.

(56) References Cited

U.S. PATENT DOCUMENTS

| 180,132 A | * | 7/1876 | Hoard et al. ............. B65D 1/04 215/6 |
| 6,301,812 B1 | * | 10/2001 | Klunk ..................... G09F 11/21 283/117 |

(Continued)

FOREIGN PATENT DOCUMENTS

| EP | 1536397 A1 | 6/2005 |
| FR | 1043230 | 11/1953 |
| WO | 2008042701 A2 | 4/2008 |

*Primary Examiner* — Nathan R Price
*Assistant Examiner* — Melissa A Snyder
(74) *Attorney, Agent, or Firm* — McDonnell Boehnen Hulbert & Berghoff LLP

(57) ABSTRACT

The present invention relates to a drug delivery device for dispensing of a dose of a medicinal product, comprising:
  a housing having at least one housing component (100; 200; 300)
  a cartridge comprising the medicinal product,
  a dose dispensing mechanism operably engaged with the cartridge for setting and/or dispensing of a predefined dose of the medicinal product, and
  a display element (102; 202; 302) being movably disposed relative to the at least one housing component (100; 200; 300), wherein
the display element (102; 202; 302) and the housing component (100; 200; 300) are mutually moveable for selectively concealing and/or revealing information provided on the display element (102; 202; 302).

11 Claims, 6 Drawing Sheets

(52) U.S. Cl.
CPC ............ *G09F 3/0295* (2013.01); *G09F 3/205* (2013.01); *G09F 11/30* (2013.01); *A61M 5/3129* (2013.01); *A61M 2005/3125* (2013.01)

(56) References Cited

U.S. PATENT DOCUMENTS

| | | | |
|---|---|---|---|
| 6,360,462 B1 * | 3/2002 | Mengel | 40/310 |
| 8,104,202 B2 * | 1/2012 | Alipour | 40/310 |
| 2002/0090980 A1 | 7/2002 | Wilcox et al. | |
| 2004/0045856 A1 * | 3/2004 | Rhoades | 206/459.5 |
| 2006/0061555 A1 | 3/2006 | Mullen | |
| 2007/0031619 A1 * | 2/2007 | Mirabell et al. | 428/34.1 |
| 2008/0171995 A1 * | 7/2008 | Vitullo | A61M 5/28 604/187 |
| 2009/0002185 A1 * | 1/2009 | Chu | 340/666 |

* cited by examiner

DRUG DELIVERY DEVICE WITH INTEGRATED EXTENDABLE/RETRACTABLE INFORMATION DISPLAY ELEMENT

CROSS REFERENCE TO RELATED APPLICATIONS

The present application is a 35 U.S.C. 371 National Application of PCT/EP2010/053966 filed Mar. 26, 2010, which claims priority to European Patent Application No. 09004571.7, filed Mar. 30, 2009, and also claims priority to U.S. Provisional Patent Application No. 61/169,849, filed Apr. 16, 2009, the entire contents of which are incorporated entirely herein by reference.

FIELD OF THE INVENTION

The present invention relates to drug delivery devices and in particular to pen-type injectors, wherein a medicinal product can be administered.

BACKGROUND AND PRIOR ART

User operated drug delivery devices are as such known in the prior art. They are typically applicable in circumstances, in which persons without formal medical training, i.e. patients, need to administer an accurate and predefined dose of a medicinal product, such as heparin, insulin or the like. In particular, such devices have application, where the medicinal product is administered on a regular or irregular basis over a short-term or long-term period.

In order to accommodate with these demands, such devices have to fulfil a number of requirements. First of all, the device must be robust in construction, yet easy to use in terms of handling and in understanding by the user of its operation and the delivery of the required dose of medicament. The dose setting and dose dispensing must be easy, intuitive and unambiguous. Further, the device should be inexpensive to manufacture and unproblematic to dispose.

Such a pen-type injector is for instance generally illustrated in EP 1 913 967 A2. This drug delivery device comprises a dose display mechanism allowing the user to select multiple doses of an injectable drug and for dispensing of the set dosage of the drug and applying said drug to a patient.

Even though such known drug delivery devices provide easy and intuitive appliance, depending on their acquirements and skills, the end users of such devices may still require support in order to handle such drug delivery devices in a proper and safe way.

Typically, drug delivery devices are supplied together with an instruction manual, for that the user is capable to inform itself about the functionality and features of the respective drug delivery device. In practice, such instruction manuals may easily get lost, in particular during a long-term use of refillable or reusable drug delivery devices. In such cases, where the instruction manual for the device or other device- or medicinal product-related information is untraceable, the risk of inappropriate handling of the drug delivery device increases. Any such inappropriate handling may imply an inappropriate and incorrect setting and dispensing of a dose, with e.g. serious consequences for the user or patient.

This endangerment even increases in such circumstances, where the patient has to deal with a plurality of different types of drug delivery devices or in cases, where a person other than the patient has to administer a predefined dose.

OBJECT OF THE INVENTION

It is therefore an object of the invention, to provide an improved drug delivery device for dispensing of a dose of a medicinal product, which is particularly easy and secure in handling. It is a further object of the invention to provide an effective means for permanently informing the user of proper and unambiguous device handling as well as to provide product related or therapy related information. Moreover, the drug delivery device should be inexpensive in production and should further be mechanically stable and robust.

SUMMARY OF THE INVENTION

The present invention provides a drug delivery device for dispensing of a dose of a medicinal product. The drug delivery device comprises a housing having at least one housing component. The device further comprises a holder for a cartridge or a cartridge, the cartridge contains the medicinal product to be dispensed by the drug delivery device, respectively. Moreover, the device has a dose dispensing mechanism, which is operably engageable with the cartridge for setting and/or for dispensing of a predefined dose of the medicinal product. In typical embodiments, the cartridge comprises a piston, to interact with a moveable piston rod of a dose dispensing mechanism. Likewise, there are further embodiments conceivable, wherein the interaction between dose dispensing mechanism and cartridge is based on a different principle.

In distal direction, i.e. in the direction pointing towards the patient, the cartridge is typically to be connected with a needle, a cannula, an infusion tube or similar delivery utensils. The cartridge itself may be designed as replaceable or disposable ampoule, cartridge, carpule or syringe. In such embodiments, wherein the cartridge comprises a piston, said piston is typically displaceable in distal direction, in order to expel a predefined dose of medicinal product from the cartridge.

The drug delivery device further comprises a display element, which is movably disposed relative to the at least one housing component. The display element and the housing component are mutually moveable for selectively concealing or covering and/or for selectively revealing information provided on the display element.

Preferably, the information provided on or provided by the display element is informative on the proper appliance of the drug delivery device. Additionally or alternatively, the information provided by the display element can be informative on the medicinal product contained in the cartridge. Further, the display element may also provide information and instructions referring to a temporal dose dispensing pattern, a patient may have to adhere.

The display element for providing medicinal product-related or device-related information is preferably non-detachably connected to the drug delivery device. In this way, it can be assured, that important information regarding proper device handling may not get lost, even when the device is in use for a long period of time. Due to a relative movement of the display element and the housing component, the invention provides an information revealing mechanism, which is adapted to provide the required information only on demand. Otherwise, the device- or product related information can be covered, concealed or hidden. By concealing the display element, the general outer appearance and design of the drug delivery device may not be impaired by the information carrying display element. Additionally, by providing a cover for the display element, the information provided on or by the display element can be protected against scuff and wear, thus, increasing the durability of the information.

According to a first embodiment of the invention, the housing component comprises a substantially sleeve-like geometry and the display element is moveable in direction substantially perpendicular or parallel to the sleeve's long axis for revealing and/or concealing the information. Hence, the housing component comprises an essentially tubular structure of circular or oval cross-section. Alternatively, the housing component interacting with the display element may also comprise a rectangular or quadratic cross-section.

The magnitude of relative movement between display element and housing component may be determined by the space required by the information. Preferably, the information is represented in graphic, pictorial or written form and may be arranged in such an order, that information may be successively seized already during a relative movement between display element and the housing component.

If for instance, the display element is moveable parallel to the long axis of the housing, the information can be preferably arranged in transverse direction. In the opposite case, where the display element is moveable in transverse direction with respect to the housing component's long axis, the units of information, either in pictorial, graphic or written form are preferably adjacently arranged parallel to the housing component's long axis. In this way, at least part of the information provided by the display element can be seized as soon as display element and housing component have moved with respect to each other about a distance that corresponds to the space required by the respective information unit.

In another aspect, the display element is foldably and/or rollably disposed inside the housing component. In this embodiment, the display element is flexible and typically comprises a sheet-like structure allowing to fold or to roll up the display element. In this way, the relative movement between display element and housing component also comes along with a mechanical deformation of the display element itself.

In particular, in a foldable configuration, the display element may be rigidly attached to the housing component with one end section, whereas the opposite end section, preferably a free end section, is subject to a relative movement with respect to the housing component. By implementing the display element as foldable and/or rollable, the space required to accommodate the display element can be kept at a minimum, whereas its information containing surface may be enlarged. By means of folding or coiling up, the display element can be easily embedded into the housing component.

According to a further preferred embodiment of the invention, the display element is rolled up on an inner sleeve being rotatably mounted in the housing component. Here, the inner sleeve and the housing component comprise mutually corresponding geometries, wherein the inner sleeve is slightly reduced in cross-section compared to the housing component. The display element may comprise a rollable sheet-like structure and may be rigidly attached to the inner sleeve with one end section, while another, opposite end section of the sheet-like display element is free to move relative to the housing component. In this way, the display element is adapted to be drawn out of the housing component in order to reveal its information.

Preferably, the display element is to be rolled up on the outer circumference of the inner rotatable sleeve, so that in an initial position, in which the display element and its information is concealed or covered by the housing component, the display element is rolled up between the inner sleeve and the housing component.

In an advanced embodiment, the housing component comprises a longitudinal slit to be intersected by at least a free end section of the display element. The slit preferably extends parallel to the housing component's or inner sleeve's long axis. Since the display element is adapted to extend through this slit, an unrolling of the display element can be achieved by gripping and drawing a free end section of the display element protruding from the housing. Therefore, it is intended, that the free end section of the display element is at least partially accessible even if the display element is almost entirely rolled up on the inner sleeve.

According to another embodiment of the invention, the display element is foldably disposed in a receptacle at the outer circumference of the housing component. The receptacle of the housing component typically has an opening, which allows to unfold and to extract the folded display element in order to reveal or to disclose its information content. The receptacle typically opens radially outwardly with respect to the substantially sleeve-like housing component. However, in alternative embodiments, it is also conceivable, to arrange the receptacle and its foldable display element at a proximal axial end section of the housing component.

In order to be foldable in a well-defined way, the display element comprises a number of fold lines, along which adjacent sections of the display element may be folded onto each other. The fold lines preferably extend in longitudinal direction, hence substantially parallel to the housing component's long axis.

By implementing a receptacle at the housing component's outer circumference, the cross-section of the housing component may deviate from a circular geometry. Depending on the geometry of the receptacle, which may be rectangular, the overall geometry of the housing component may vary correspondingly. However, such an embodiment comes along with the benefit, that the implementation of the display element has almost no effect on the inner configuration and dimensions of the housing component. In this way, those components to be disposed inside said housing component may remain unaltered compared to embodiments as they are known in the prior art.

The receptacle for receiving the folded display element may be integrally formed with the housing component. Alternatively, it may be designed as a separate component to be attached to the housing component.

According to a further preferred embodiment of the invention, the display element comprises a gripping element at its free end section. In this way, gripping of the free end of the display element is facilitated, especially in order to unroll or to unfold the display element into an information revealing configuration. The gripping element may comprise a bar- or rail-like geometry. In preferable embodiments, the gripping element may abut against the outer surface of the housing component when the display element is in its concealed or covered initial configuration.

The gripping element may have a longitudinal extension comparable to the length of the housing component's slit or the receptacle's opening. In this way, the display element can be easily gripped anywhere along the housing's slit or the receptacle's opening.

In another aspect of the invention, the display element comprises a lid at its free end section to cover a receptacle or a slit of the housing component. The lid and the gripping element may be implemented in a single common piece having for instance a T-shaped cross-section, wherein a portion extending laterally across the slit or opening serves as a lid and wherein an adjacent portion protruding in radial direction serves as gripping element. Preferably, the combined lid and gripping element is rigidly attached to the free end of the flexible display element. The transverse lid portion may further serve as a seal in order to protect the inside of the receptacle or the inside of the housing component against environmental influences, such as dust and humidity.

According to another embodiment of the invention, the housing component and the display element comprise corresponding sleeve-like geometries. They are further slidably disposed with respect to each other along the sleeve's long axis.

Moreover, the two sleeves, display element and housing component are concentrically arranged in an interleaved manner. Preferably, the display element comprises information at its outer surface and has a smaller transverse diameter than the housing component, which is adapted to receive the display element. In this way, the information provided by the display element can either be revealed by slidably moving the display element relative to the housing component or by slidably moving the housing component relative to the display element, depending on whether the housing component or the display element is designed as axially moveable component.

According to a further preferred embodiment, the display element and the housing component comprise at least one longitudinal rib to be engaged with the corresponding longitudinal slit. In this way, a relative rotation between housing component and display element with their common longitudinal axis as axis of rotation can be effectively prevented. The longitudinal and radially protruding rib may either be arranged at the display element's outer circumference or it may be arranged at the inner surface of the housing component in a radially inwardly pointing manner. Correspondingly, a longitudinal slit or longitudinal notch to be engaged with the protruding rib can either be disposed at a corresponding surface of the housing component or the display element.

According to a further preferred embodiment, the display element and/or the housing component is or are transferable into an information revealing configuration against a spring force, which is provided by at least one spring element. In embodiments, where the display element is to be rolled up on a rotatable inner sleeve, rotation of said sleeve may be spring biased, e.g. by means of a torsion spring. By means of such a spring element, a drawn out display element may roll up autonomously as soon as a counter acting tension is no longer applied to the display element in radial outward direction.

Also, foldable embodiments of the display element can be combined with spring elements, which may be embedded into the foldable display element in order to provide an autonomous folding up. Additionally, also an axial movement of sleeve-like display element and housing component can be counteracted by an appropriate spring element so as to return the two components into an initial configuration in which the information is concealed or covered by the housing component.

According to a further preferred embodiment of the invention, the display element is printed with printed information, such as graphical and pictorial illustrations, pictograms and written words. For instance, the display element may comprise a tear-resistant sheet, e.g. made of paper, in particular coated or laminated paper or similar substrates on cellulose basis. Alternatively, the display element may comprise a printable and printed sheet material on polymer basis.

According to a further embodiment, the display element comprises an electronic paper display, adapted to mimic the appearance of ordinary ink on paper. It may be adapted as electrophoretic display, which is able to form visible images by rearranging charged pigment particles due to the application of an electric field. Other conceivable electronic paper display elements making use of the principle of electrowetting display technology, that are based on controlling the shape of a confined water-oil interface by an applied voltage are also conceivable.

Such electronic paper displays may further be reconfigurable on demand and may provide a long lasting and durable information pattern, with negligible or even without electric power consumption.

In a further embodiment, the electronic paper display may be adapted to reconfigure itself according to its absolute orientation with respect to ground. The device may therefore be equipped with some kind of orientation-, positioning- or gravity-sensor, providing information on the momentary orientation of the device. According to this position information, the display may reconfigure to arrange textual or figural information in such a way, that the reading direction is or remains substantially perpendicular to the momentary direction of gravity. Consequently, when a user tilts the device, the displayed information will tilt accordingly with respect to the device. In this way, the information to be displayed by the electronic paper display remains upright and readable for the user, irrespective of the momentary orientation of the device.

The term "medicinal product", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, a antibody, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly- Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane such as hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be apparent to those skilled in the art, that various modifications and variations can be made to the present invention without departing from the spirit and scope of the invention. Further, it is to be noted, that any reference signs used in the appended claims are not to be construed as limiting the scope of the present invention.

BRIEF DESCRIPTION OF THE DRAWINGS

Without limitation, the present invention will be explained in greater detail below in connection with preferred embodiments and with reference to the drawings in which.

DETAILED DESCRIPTION

Figure 1:
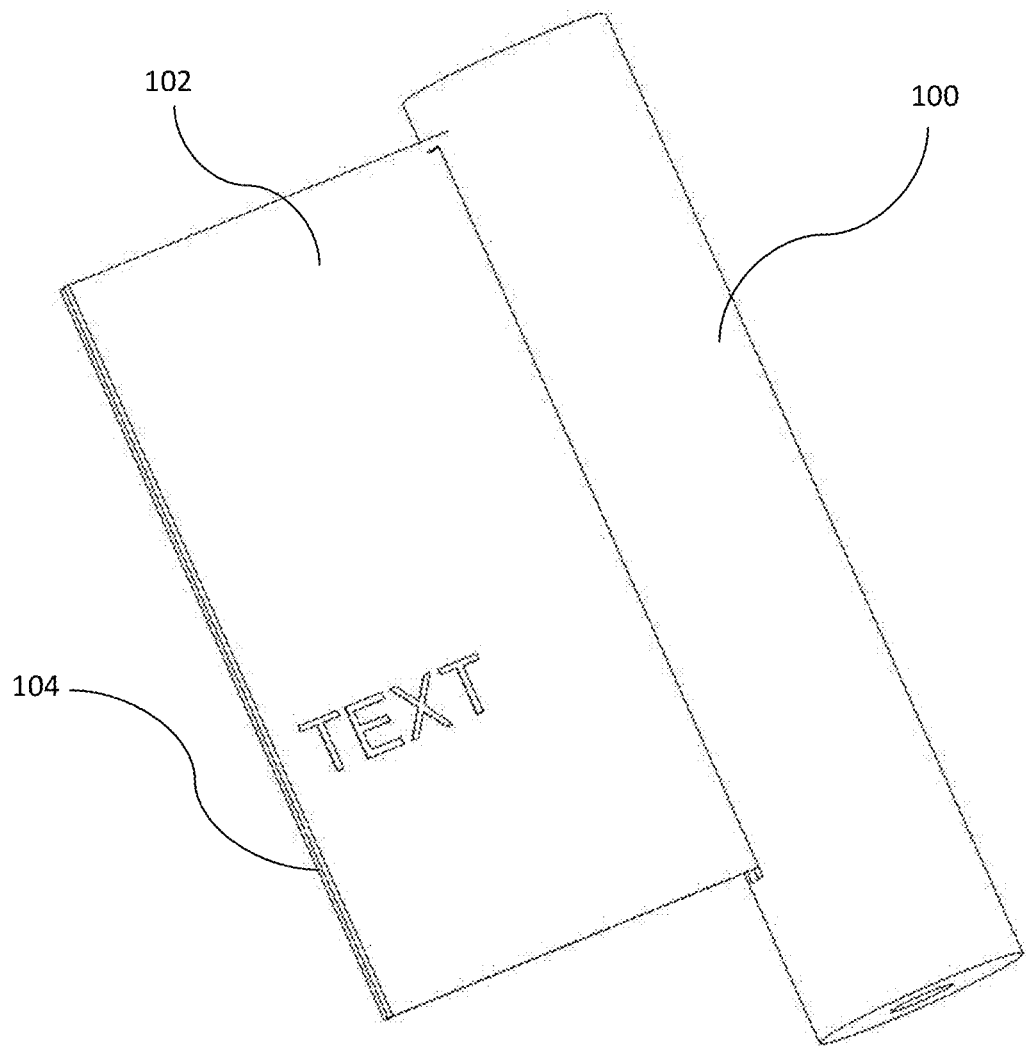
FIG. 1 schematically illustrates a first embodiment of the invention with a rollable display element in a perspective view FIG. 2 in a cross sectional illustration schematically shows illustrates the embodiment according to FIG. 1 with a rolled up display element, FIG. 3 schematically depicts a second embodiment of the invention with interleaved sleeve-like display element and housing component.
Figure 2:
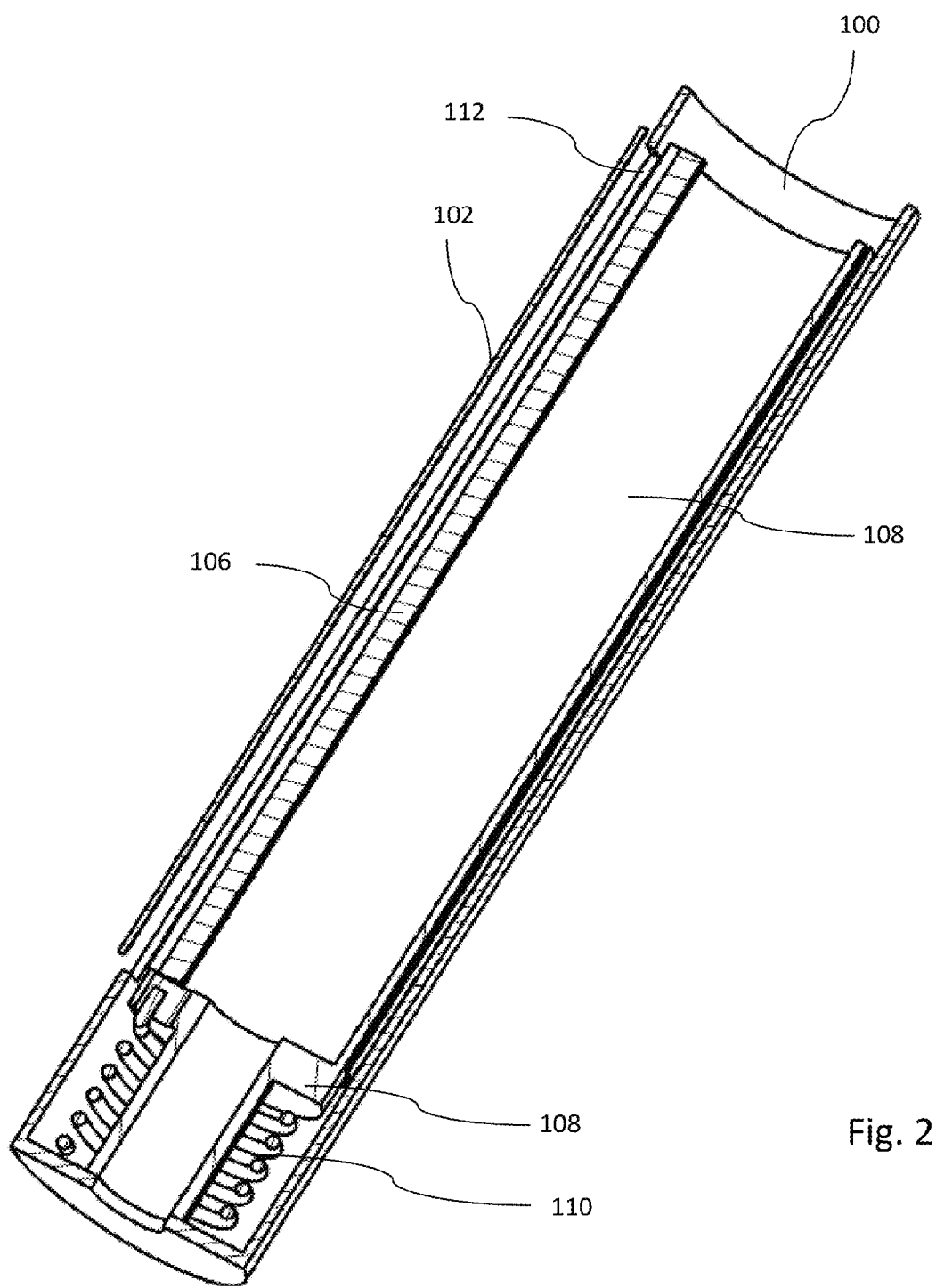

In FIGS. 1 and 2, a first embodiment of the invention is illustrated. A housing component 100, which may either serve as housing for a dose dispensing mechanism or as a cartridge retaining part of a housing of a drug delivery device houses a rotatably mounted inner sleeve 108. The housing element 100 and the inner sleeve 108 have a circular cross-section, such that the inner sleeve 108 is free to rotate around the sleeves' 100, 108 long axes.

The display element 102 has a sheet-like contour and geometry is adapted to be rolled up on the inner sleeve 108 as illustrated in FIG. 2. Hence, in the rolled up configuration according to FIG. 2, the flexible and rollable display element 102 is wrapped around the outer circumference of the inner sleeve 108.

The housing component 100 further comprises at least a longitudinal slit 112, as illustrated in FIG. 2, allowing the display element 102 to be drawn off in radial direction. For this purpose, at its free end section, the display element 102 comprises a gripping element 104, having a bar or rail-like structure and which extends substantially in longitudinal direction. As can further be seen from the cross-sectional illustration of FIG. 2, the inner sleeve 108 is spring biased with respect to the housing component 100. Hence, by exerting a radially outwardly directed force to the gripping element 104, the display element 102 unfurls accompanied by a respective rotation of the inner sleeve 108 leading in turn to an increase of a restoring force of the spring element 110.

Once the display element 102 has been drawn off from the housing component 100, as illustrated in FIG. 1, the inner sleeve 108 may rotate in opposite direction under the effect of the spring element 110 for autonomously rolling up the display element 102.

The display element 102 itself may be implemented as printable and printed information sheet or as printed information log. The sheet 102 may be of cellulose or polymer basis and may be coated or laminated, such that the printed information remains durable on the display element 102. The printed information may be informative on the type of the medicinal product contained in a cartridge of the drug delivery device.

Further the display element 102 may provide information on proper usage of the drug delivery device. It may provide an extensive or abbreviated instruction manual of the drug delivery device. Further, the display element 102 may provide patient- or therapy-related information that might be useful and necessary for appropriate and safe appliance of the drug delivery device.

As can be further seen in FIG. 2, also the inner sleeve 108 comprises a longitudinal slit, which is adapted to receive an end section and/or a fixing element 106 of the display element 102. The fixing element 106 is typically designed as a type of welting being rigidly connected or bonded to the display element's sheet 102. By slidingly introducing the respective end section of the display element 102 into said slit of the inner sleeve 108, the sheet-like display element 102 can be rigidly attached to the inner sleeve 108 at least with respect to a transverse movement.

Since the fixing element 106 is larger in size than the inner sleeve's 108 slit, by pulling the gripping element 104 radially outwardly, the unrolling of the display element 102 leads to a respective rotation of the inner sleeve 108 against the action of the spring element 110.

Figure 3:
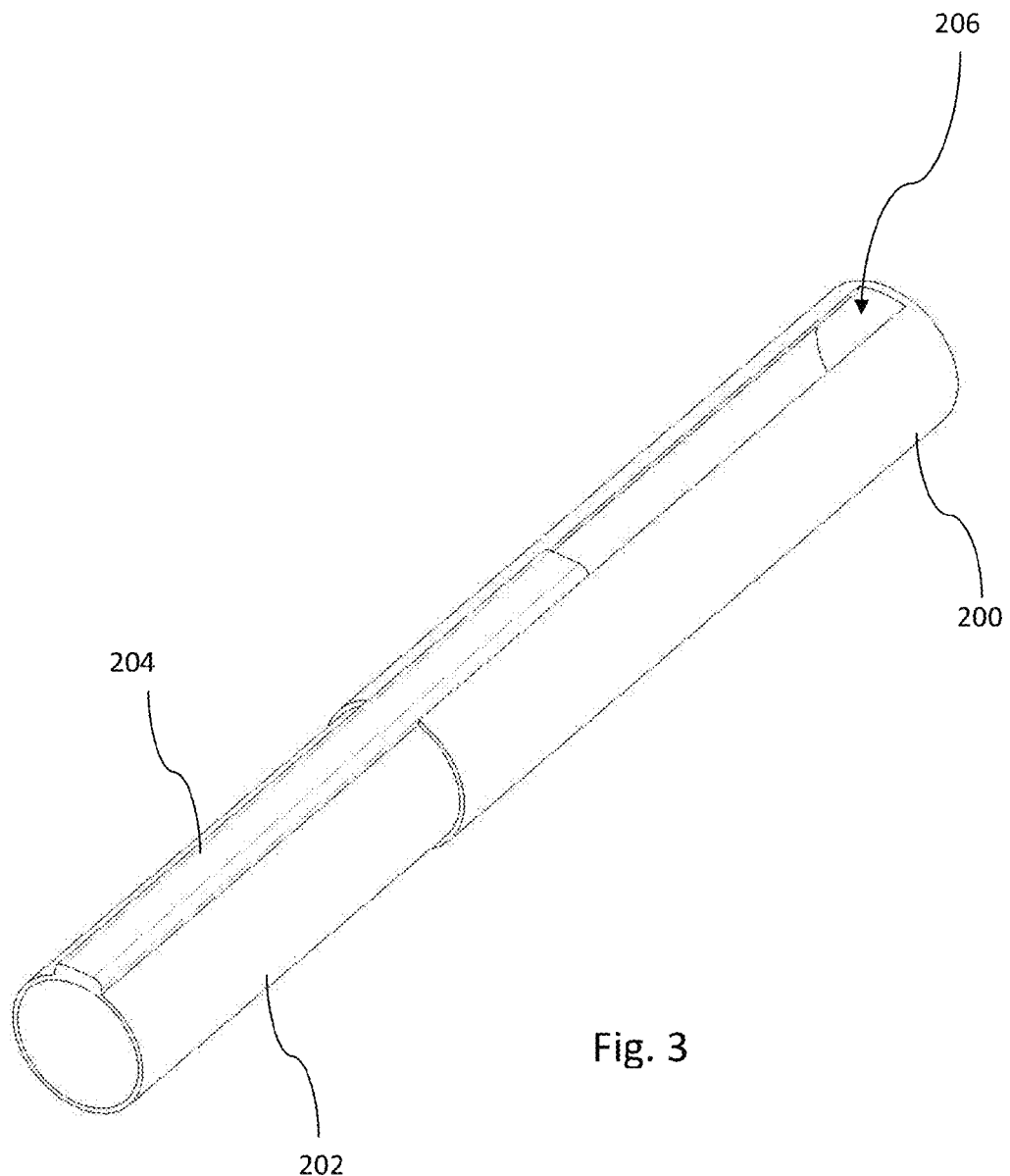

The second embodiment according to FIG. 3 exemplary shows a display element 202 comprising a rather stiff and non-flexible behaviour. Here, the display element 202 comprises a sleeve-like geometry with a radially outwardly protruding rib 204. The display element 202 is slidably disposed relative to the housing component 202. This interleaved arrangement allows for a relative axial displacement in order to reveal or to conceal the information provided on the outer circumference of the display element 202.

In this embodiment, the display element 202 itself may act as a housing component, whereas the housing component 200 may serve as a slidable cover for the information printed on the display element 202. In this embodiment, either one of display element 202 or housing component 200 may be connected to a further, not particularly illustrated housing component of the drug delivery device, which for instance contains a dose dispensing mechanism (not illustrated) or a cartridge filled with the medicinal product (not illustrated).

Furthermore, the radially protruding rib 204 of the display element 202 engages with a slit or notch 206 of the housing component 200. In this way, a relative rotation between display element 202 and housing component 200 with their longitudinal axis as axis of rotation can be effectively prevented. By means of the mutually engaging components, rib 204 and slit or notch 206, a relative axial sliding displacement between these two sleeve-like components 202, 200 can be realized.

Figure 4:
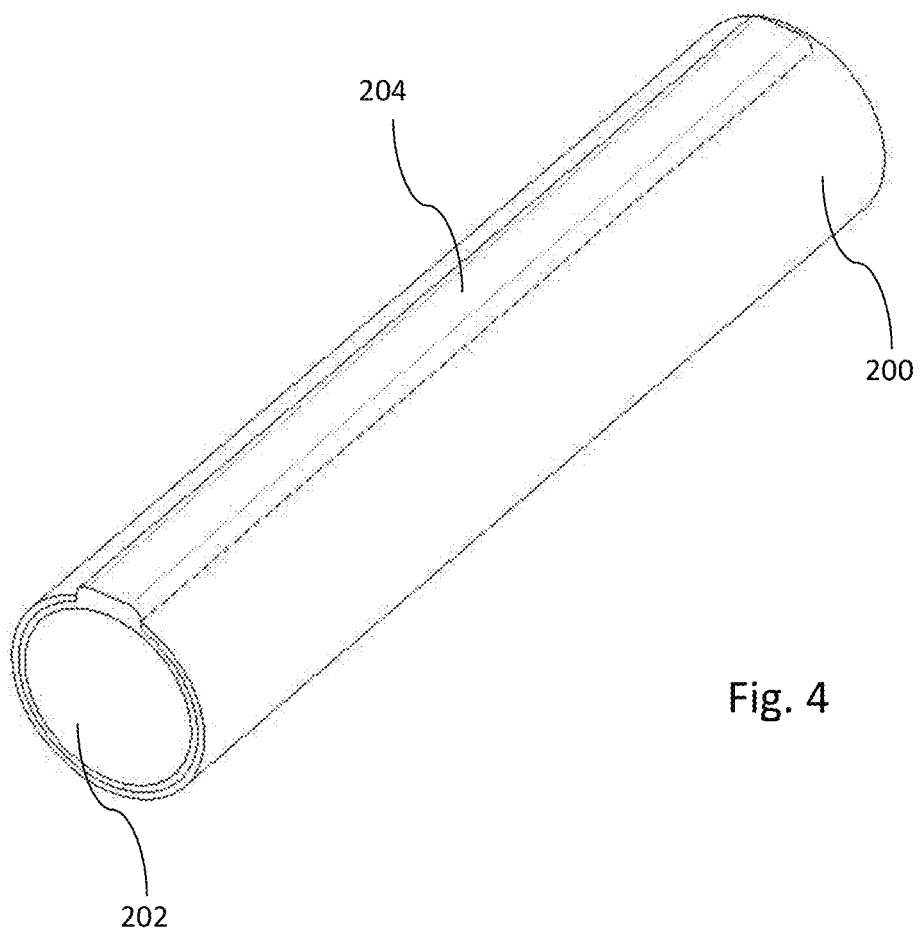
FIG. 4 shows the embodiment according to FIG. 3 with its display element in its initial, concealed configuration, FIG. 5 schematically depicts a third embodiment of the invention with a foldable display element in unfolded configuration

In FIG. 4, the display element 202 is in its initial position, in which it is entirely concealed and covered by the housing component 200. Since the radially protruding rib 204 even protrudes from the outer circumference of the housing component 200, it can serve as a gripping aid for a user to slidably displace the display element 202 relative to the housing component 200.

Figure 5:
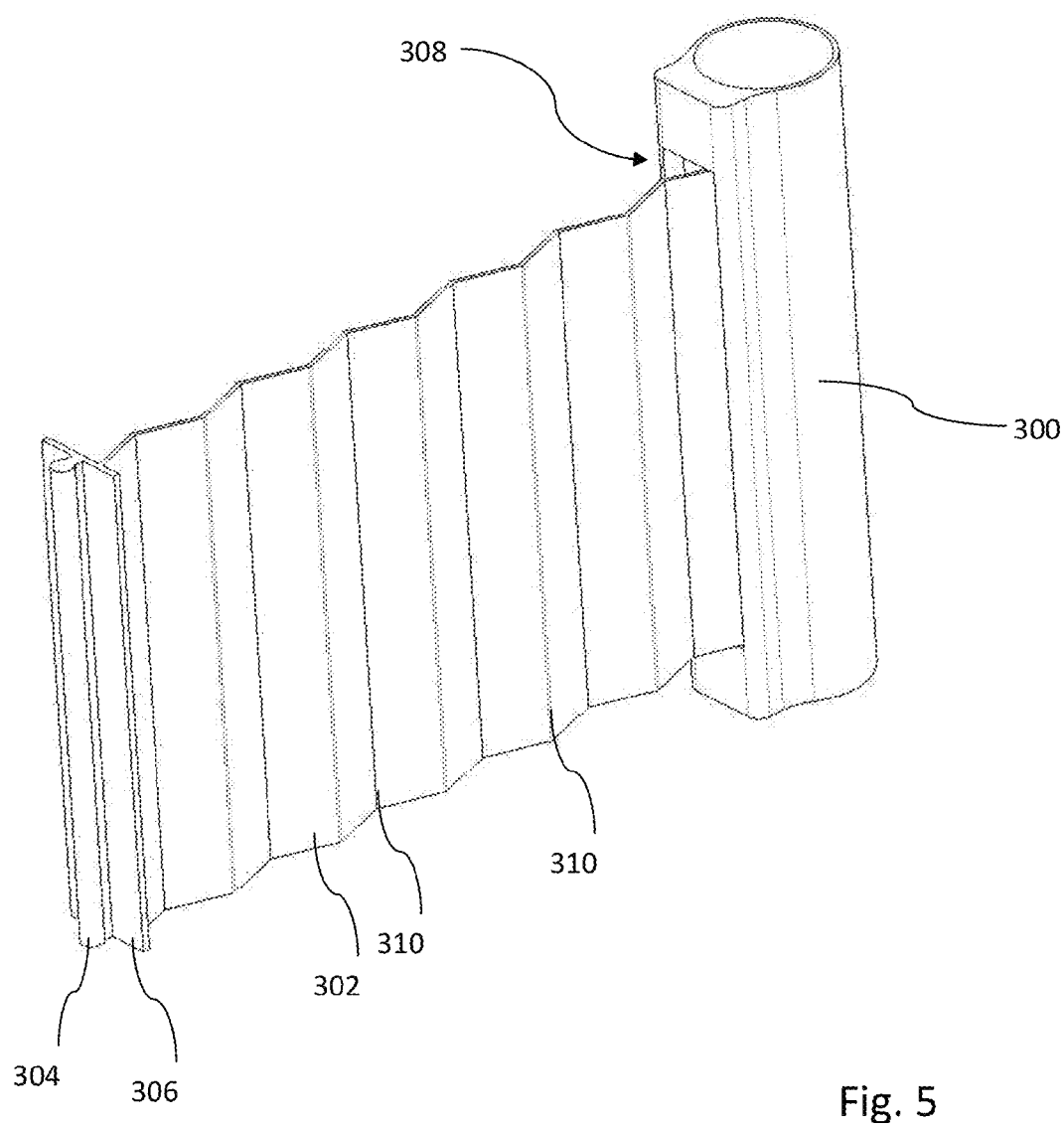
Figure 6:
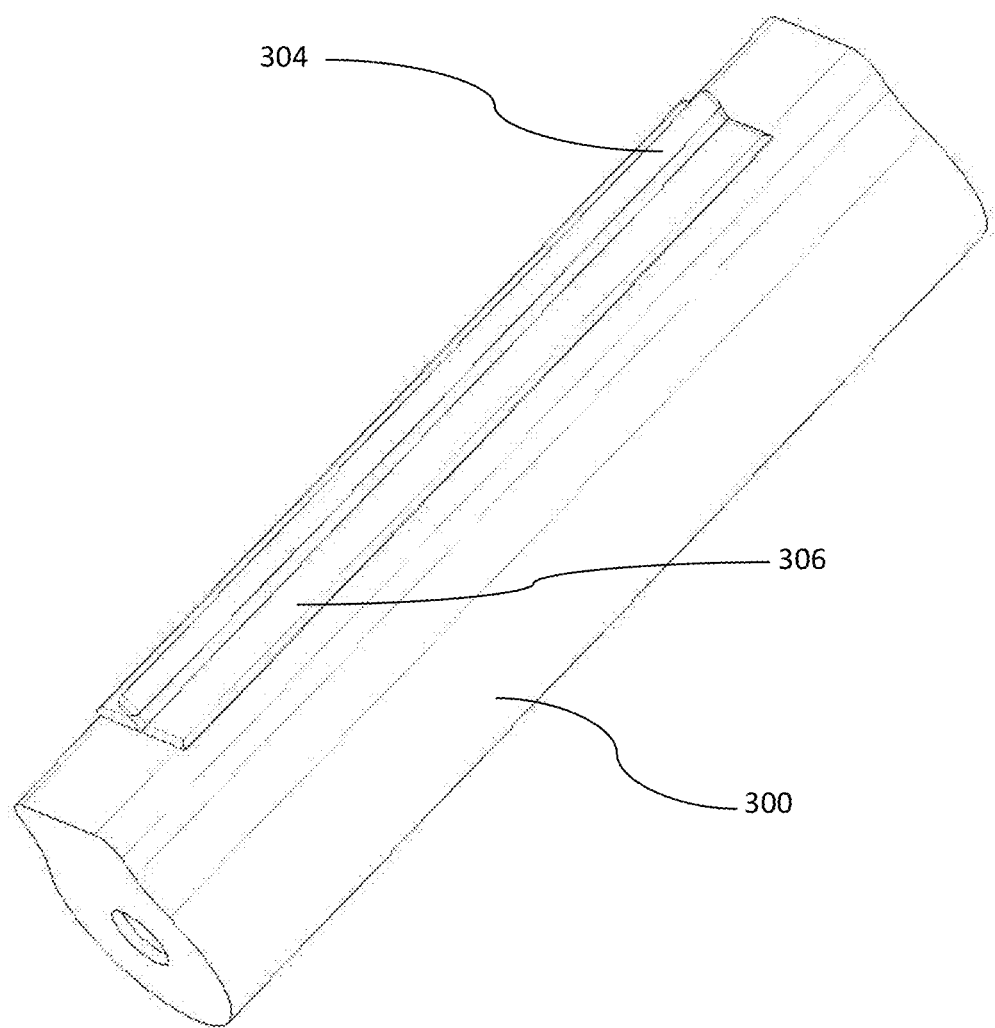
FIG. 6 illustrates the embodiment according to FIG. 5 with a folded display element.

The third embodiment illustrated in FIGS. 5 and 6 provides a foldable display element 102, that comprises regularly spaced fold lines 310 extending in longitudinal direction, i.e. parallel to the housing component's 300 long axis. Whereas the unfolded configuration is illustrated in FIG. 5, the folded and hidden configuration of the display element 302 is exemplary illustrated in FIG. 6. As can be seen, the foldable sheet-like display element 302 is adapted to be folded in a zig-zag-like manner. Consequently, adjacent sections of the display element 302 that are separated by a fold line 310 are arranged on top of each other in the folded not explicitly illustrated configuration of FIG. 6.

As can be further seen in detail in FIG. 5, the housing component 300 integrally comprises a receptacle 308 of a somewhat rectangular shape for receiving the folded display element 302. As its free end, which points away from the inner section of the housing component 300, the display element 302 is rigidly connected with a combined lid and gripping element 304, 306. This combined gripping and lid element 304, 306 has a T-shaped cross section. Here, the lid section 306 is adapted to seal the receptacle 308, whereas the gripping section 304 is adapted to be gripped by a user for the purpose of unfolding the display element 302.

Additionally, the display element 302 may comprise integrated spring elements in order to keep the display element 302 in its folded configuration. In this way, a revealing of information by drawing out of the display element 302 has to be conducted against a spring force. As soon as the gripping element 304 is released, the at least one integrated spring or pretensioning element serves to return the display element 302 in its folded configuration, as illustrated in FIG. 6.

The illustrated embodiment of mutually moveable display element and housing component are by no way restricted to a particular housing component. Generally, any longitudinal or sleeve-like housing component of a drug delivery device, such as a pen-type injector is in principle appropriate to be provided with any of the illustrated display elements and appropriate reveal and conceal mechanisms, no matter on whether the housing component 100, 200, 300 is implemented as cartridge retaining part, pen cap or as a housing component adapted to house a dose dispensing mechanism of the drug delivery device.

LIST OF REFERENCE NUMERALS 100 housing
102 display element
104 gripping element
106 fixing element
108 inner sleeve
110 spring element
112 slit
200 housing
202 display element
204 protrusion
206 slit
300 housing
302 display element
304 gripping element
306 lid
308 receptacle
310 fold lines

The invention claimed is:

1. An injection drug delivery device for dispensing of a dose of a medicinal product, comprising:
a housing having at least one housing component,
a holder for a cartridge, the cartridge comprising the medicinal product,
a dose dispensing mechanism operably engaged with the cartridge for setting and/or dispensing of a predefined dose of the medicinal product, wherein the housing component serves as a housing for the dose dispensing mechanism, and
a spring biased display element movably disposed inside the at least one housing component,
an inner sleeve coupled to a helical spring and rotatably mounted in the housing component,
wherein the display element comprises a fixing element,
wherein the inner sleeve comprises a longitudinal slit adapted to receive the fixing element of the display element, and wherein the fixing element is larger in size than the longitudinal slit,
wherein the display element is moveable for selectively concealing and/or revealing information provided on the display element as the display element is moved into and out of the housing component,
wherein the display is rolled up on the inner sleeve, and wherein the inner sleeve is configured to surround at least a portion of the dose dispensing mechanism.

2. The drug delivery device according to claim 1, wherein the housing component comprises a substantially sleeve-like geometry and wherein the display is movable in direction substantially perpendicular or parallel to the sleeve's long axis for revealing the information.

3. The drug delivery device according to claim 1, wherein the housing component comprises a longitudinal slit intersected by at least a free end section of the display.

4. The drug delivery device according to claim 1, wherein the display comprises a gripping element at its free end section.

5. The drug delivery device according to claim 1, wherein the display comprises a lid at its free end section to cover a receptacle or slit of the housing component.

6. The drug delivery device according to claim 1, wherein the display comprises information at its outer surface and has a smaller transverse diameter than the housing component, which is adapted to receive the display.

7. The drug delivery device according to claim 1, wherein the display and the housing component comprise at least one longitudinal rib to be engaged with a corresponding longitudinal slit or notch.

8. The drug delivery device according to claim 1,
wherein the display and/or the housing component are transferable in an information revealing configuration against a spring force provided by at least one spring element.

9. The drug delivery device according to claim 1, wherein the display is printed with printed information.

10. An injection drug delivery device for dispensing of a dose of a medicinal product, comprising:
a housing having at least one housing component,
a holder for a cartridge, the cartridge comprising the medicinal product,
a dose dispensing mechanism operably engaged with the cartridge for setting and/or dispensing of a predefined dose of the medicinal product, wherein the housing component serves as a housing for the dose dispensing mechanism, and
a display element movably disposed inside the at least one housing component, wherein the housing component and the display element comprise corresponding sleeve-like geometries and are slidably disposed with respect to each other along a long axis of the at least one housing component, wherein the display element and the housing component are moveable with respect to one another for selectively concealing and/or revealing information provided on the display element as the display element is slid into and out of the housing component.

11. The drug delivery device according to claim 10, wherein the housing component and the display comprise corresponding sleeve-like geometries and are slidably disposed with respect to each other along the sleeve's long axis.

\* \* \* \* \*